US012186129B2

(12) United States Patent
Chumo et al.

(10) Patent No.: US 12,186,129 B2
(45) Date of Patent: Jan. 7, 2025

(54) DEVICES AND METHODS FOR ULTRASOUND IMAGING

(71) Applicant: Boston Scientific Scimed, Inc., Maple Grove, MN (US)

(72) Inventors: Benedicta Chumo, Framingham, MA (US); Mollie Knake, Bellevue, IA (US); Shawn Kerr, Lancaster, MA (US); Alissa Brandon, Cambridge, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1875 days.

(21) Appl. No.: 15/073,749

(22) Filed: Mar. 18, 2016

(65) Prior Publication Data

US 2016/0287210 A1 Oct. 6, 2016

Related U.S. Application Data

(60) Provisional application No. 62/140,564, filed on Mar. 31, 2015.

(51) Int. Cl.
*A61B 8/12* (2006.01)
*A61B 1/018* (2006.01)
(Continued)

(52) U.S. Cl.
CPC ............. *A61B 8/12* (2013.01); *A61B 1/018* (2013.01); *A61B 8/445* (2013.01); *A61B 8/4461* (2013.01); *A61B 8/4494* (2013.01); *A61B 8/0841* (2013.01)

(58) Field of Classification Search
None
See application file for complete search history.

(56) References Cited

U.S. PATENT DOCUMENTS 5,386,818 A * 2/1995 Schneebaum .......... A61B 1/018
600/104
6,193,666 B1 2/2001 Ouchi
(Continued)

FOREIGN PATENT DOCUMENTS

| JP | 2001104315 A | 4/2001 | |
| WO | WO 2009/029639 A1 * | 3/2009 | ............. A61B 17/58 |
| WO | 2010048208 A1 | 4/2010 | |

OTHER PUBLICATIONS

Olympus, "Endoscopic Ultrasonic Probes: A Wide Range of Ultrasonic Probes Enhances EBUS Versatility", Japan (4 pages).
(Continued)

*Primary Examiner* — Katherine L Fernandez
*Assistant Examiner* — Michael S Kellogg
(74) *Attorney, Agent, or Firm* — Seager, Tufte & Wickhem, LLP (57) ABSTRACT

Methods and devices for generating ultrasound images during a medical procedure are disclosed. The device may comprise a shaft that includes a working channel for receiving an instrument, the working channel extending from a proximal end of the shaft to a distal end of the shaft, and an ultrasound sensor disposed radially outward of a distal portion of the working channel such that the ultrasound sensor at least partially surrounds the working channel. The ultrasound sensor may be configured to image a single field of view greater than about 90 degrees about the shaft, e.g., simultaneously, while conducting a medical procedure with an instrument inserted through the working channel.

20 Claims, 5 Drawing Sheets

(51) Int. Cl.
*A61B 8/00* (2006.01)
*A61B 8/08* (2006.01)

(56) References Cited

U.S. PATENT DOCUMENTS

| | | |
|---|---|---|
| 2011/0190662 A1 | 8/2011 | McWeeney |
| 2011/0319714 A1* | 12/2011 | Roelle ................ A61B 1/00006 600/118 |
| 2012/0095404 A1* | 4/2012 | Massengale ....... A61B 17/3401 604/164.01 |
| 2013/0225943 A1 | 8/2013 | Holsing et al. |
| 2014/0088456 A1 | 3/2014 | Wang |
| 2014/0276615 A1* | 9/2014 | Laroya ................ A61B 8/0891 604/510 |

OTHER PUBLICATIONS

Schuhmann et al., "Endobronchial Ultrasound for Peripheral Lesions: A Review", 2013, pp. 3-6, vol. 2, No. 1, Endoscopic Ultrasound (4 pages).

* cited by examiner

DEVICES AND METHODS FOR ULTRASOUND IMAGING

CROSS-REFERENCE TO RELATED APPLICATION(S)

This patent application claims benefit of priority under U.S.C. § 119 to U.S. Provisional Patent Application No. 62/140,564, filed Mar. 31, 2015, the entirety of which is incorporated herein by reference.

TECHNICAL FIELD

Embodiments of the present disclosure relate generally to medical devices and related methods. More specifically, the present disclosure relates to devices useful in ultrasound-guided medical procedures, such as biopsy and diagnostic procedures.

BACKGROUND

Medical procedures are often complicated by a limited field of view of the treatment area, and/or by temporal delay between capturing an image of the treatment area and performing the procedure. Sonography is one example of medical imaging, wherein sound waves (ultrasound) are sent through the body to collect information on internal tissues and structures based on the time, speed, and frequency at which the sound waves are reflected. In endoscopic ultrasound (EUS), an ultrasound probe is introduced into the body for internal imaging. The tip of the probe makes contact with tissue directly or via a fluid-filled balloon to emit and detect returning sound waves for display as an image. However, the ultrasound probe usually must be exchanged for other instruments to biopsy tissue or perform other procedures at a region of interest identified via the ultrasound image. While some devices include a needle adjacent to an ultrasound transducer, e.g., for endobronchial ultrasound transbronchial needle aspiration (EBUS-TBNA), the field of view is limited and does not allow for wide-angle imaging. In addition, these devices do not allow for exchange of the needle or use of other instruments during imaging.

SUMMARY OF THE DISCLOSURE

The present disclosure includes a medical device comprising a shaft, the shaft including a working channel extending from a proximal end of the shaft to a distal end of the shaft, and an ultrasound sensor disposed radially outward of a distal portion of the working channel such that the ultrasound sensor at least partially surrounds the working channel. The working channel of the medical device may be configured to receive an instrument and maintain an orientation of the instrument with respect to the shaft. Additionally or alternatively, the working channel may have a non-circular cross-sectional area to prevent rotation of the instrument within the working channel. In some aspects, the medical device may comprise the instrument. The instrument may be translatable from the proximal end of the shaft to the distal end of the shaft. In addition or alternatively, the instrument may comprise a flexible material, and/or may have a preset curved configuration, such that a distal end of the instrument has a substantially straight configuration within the working channel and the curved configuration outside the working channel. In some aspects of the present disclosure, the shaft of the medical device may include an area having an echogenic signature distinct from a remainder of the shaft. In examples wherein the medical device comprises an instrument having a preset curved configuration, the distal end of the instrument may be radially aligned with the area while in the curved configuration.

The ultrasound sensor of the medical device may include a plurality of sensors or a single ultrasound sensor disposed about the working channel to at least partially surround the working channel. For examples of medical devices comprising a plurality of ultrasound sensors, the ultrasound sensors may be spaced at regular intervals about a perimeter of the shaft. In some aspects, the ultrasound sensor (e.g., single ultrasound sensor or plurality of ultrasound sensors) may completely surround the working channel. The ultrasound sensor (e.g., single ultrasound sensor or plurality of ultrasound sensors) may be configured to image a single field of view greater than about 90 degrees, greater than about 180 degrees, and/or may be configured to image a single field of view of about 360 degrees. In some aspects of the present disclosure, the working channel of the medical device may be a first working channel, wherein the medical device may further comprise a second working channel radially inward of the ultrasound sensor.

In some aspects of the present disclosure, the medical device may comprise a controller coupled to the proximal end of the shaft and a plurality of control members for deflecting the distal end of the shaft in at least two different planes. The plurality of control members may extend from the controller to a portion of the shaft proximal to the ultrasound sensor.

The present disclosure also includes a medical device comprising a shaft, the shaft including a working channel extending from a proximal end of the shaft to a distal end of the shaft; an ultrasound sensor radially outward of a distal portion of the working channel; and a controller coupled to the proximal end of the shaft for deflecting the distal end of the shaft in at least two different planes. In some aspects, the medical device may further comprise a plurality of control members extending from the controller to a portion of the shaft proximal to the ultrasound sensor. Additionally or alternatively, the ultrasound sensor may completely surround the working channel. In some examples, the ultrasound sensor may be configured to image a single field of view greater than about 90 degrees, greater than about 180 degrees, and/or may be configured to image a single field of view of about 360 degrees.

Medical devices according to the present disclosure may be useful in treating patients and/or conducting medical procedures. For example, the present disclosure includes a method of treating a patient comprising inserting a shaft of a medical device into a passageway of the patient, the shaft including a working channel extending from a proximal end of the shaft to a distal end of the shaft, and an ultrasound sensor disposed radially outward of a distal portion of the working channel such that the ultrasound sensor at least partially surrounds the working channel; the method further comprising generating at least one image with the ultrasound sensor. In some aspects, the method may further comprise inserting an instrument into the working channel, and manipulating the instrument to conduct a medical procedure on the passageway while generating the image.

BRIEF DESCRIPTION OF THE FIGURES

The accompanying drawings, which are incorporated in and constitute a part of this specification, illustrate various exemplary embodiments and together with the description, serve to explain the principles of the disclosed embodiments.

DETAILED DESCRIPTION

Embodiments of the present disclosure include medical devices useful in obtaining ultrasound images within the body, e.g., via one or more ultrasound sensors, and methods of performing medical procedures using such devices.

The term "ultrasound sensor" as used herein includes devices configured to transmit and/or receive ultrasound (≥20 kHz) and other frequency sound waves for producing an image. For example, ultrasound sensors suitable for the present disclosure include transceivers and transducers capable of both transmitting and receiving ultrasound. By measuring the time between sending ultrasound signals and receiving the echoes of those signals reflected by various features in the body, the distance to those features may be determined, e.g., to obtain images. The images may provide information regarding tissue structure (e.g., density, shape, contour, etc.), the presence or absence of tumors, lesions, or other abnormalities, the size and location of any such abnormalities, and/or blood flow or other fluid flow characteristics. The images may be two-dimensional or three-dimensional.

Ultrasound imaging may have advantages over other types of imaging. For example, ultrasound can provide real-time images, avoiding a delay between capturing an image of an area of interest and performing a medical procedure on that area. Further, because ultrasound sensors operate via sound waves, e.g., rather than electromagnetic radiation, they are typically less harmful to the patient.

Figure 1:
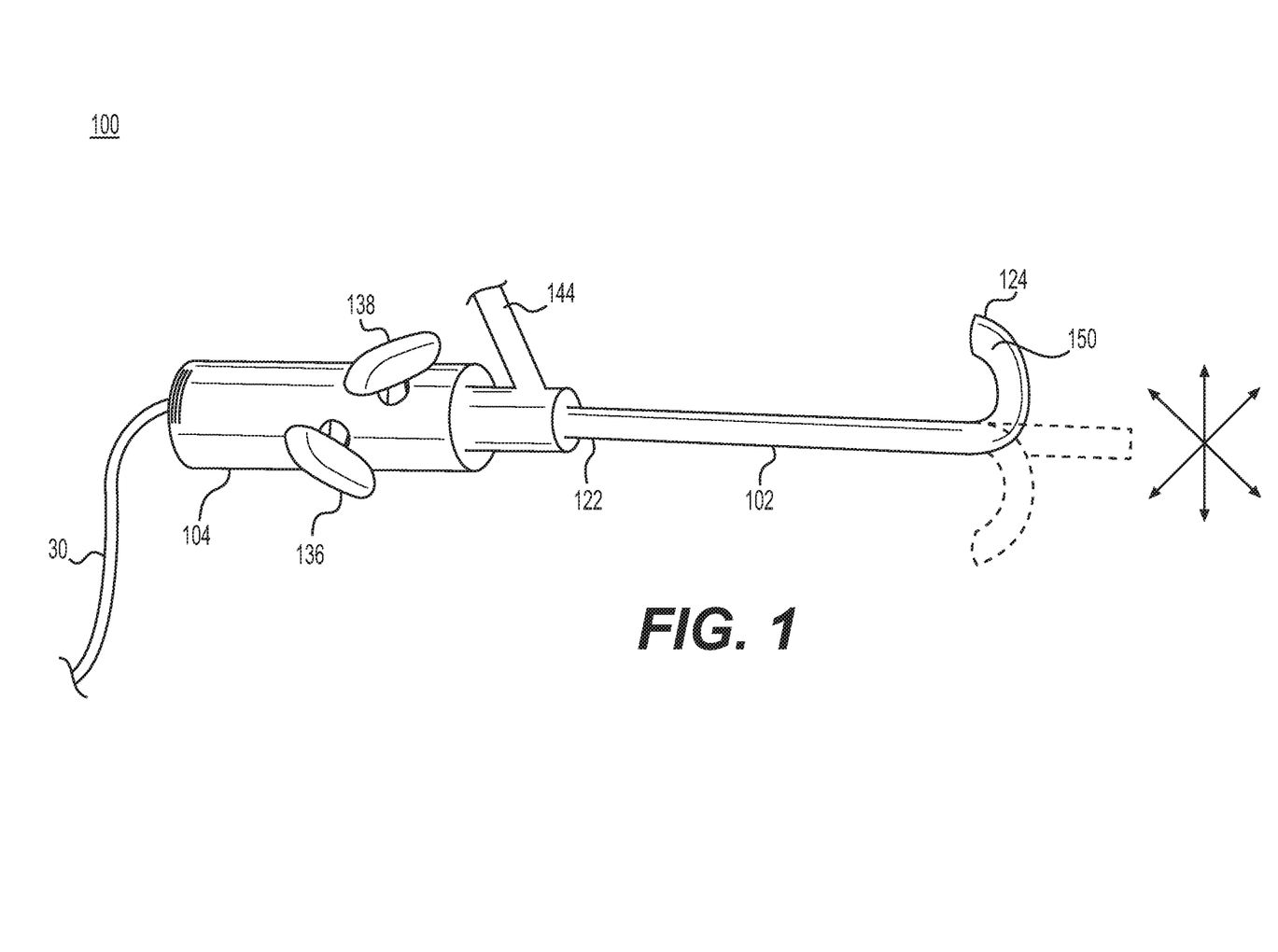
FIG. 1 shows an exemplary medical device, in accordance with one or more embodiments of the present disclosure.

FIG. 1 shows an exemplary medical device 100 according to some embodiments of the present disclosure. The medical device 100 may comprise a controller 104 and a shaft 102 extending from a proximal end 122 to a distal end 124. The controller 104 may have any suitable shape, including cylindrical and ergonomic shapes for easy or comfortable gripping by one or both hands. The shaft 102 may include one or more ultrasound sensors 150. The ultrasound sensor(s) 150 may be at or proximate to the distal end 124 of the shaft 102. The controller 104 may include an electronic cable 30, e.g., for providing power to the ultrasound sensor(s) 150 and/or for communication between the ultrasound sensor(s) 150 and a processor or graphical interface.

In some embodiments, the medical device 100 may be steerable, e.g., to allow an operator to navigate the shaft 102 through tortuous anatomy and/or towards a site of interest. Any suitable steering mechanism may be used. For example, the steering mechanism may comprise a plurality of steering wires coupling the controller 104 to the shaft 102, e.g., to transmit user input from the controller 104 to the shaft 102 to articulate or deflect the shaft 102 along one or more planes.

Figure 2A:
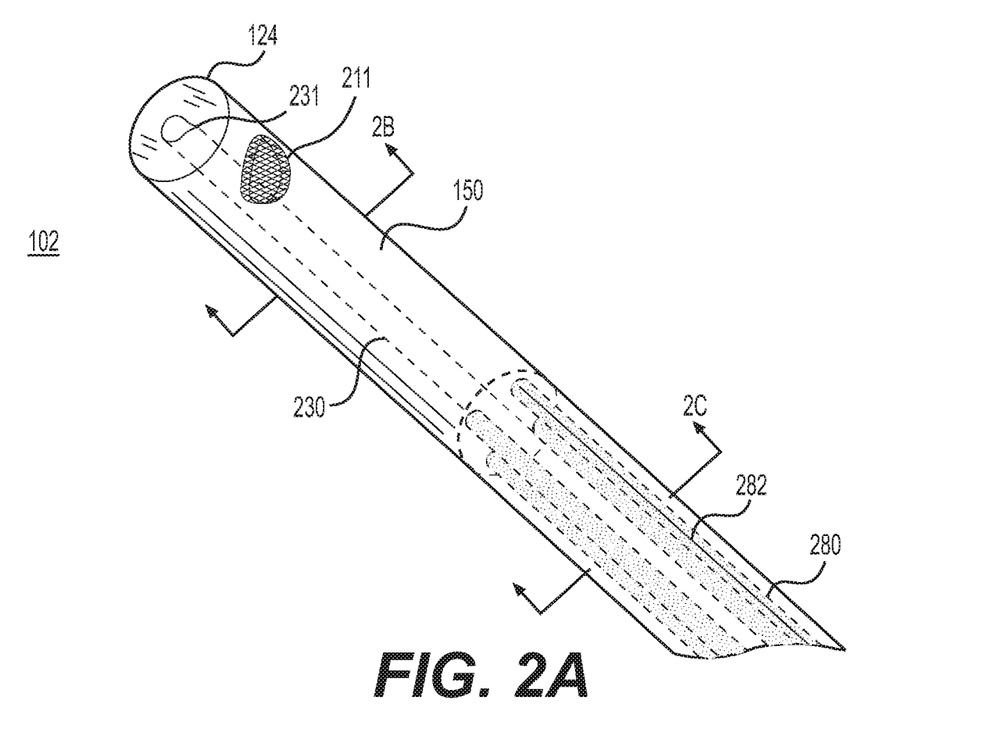
FIG. 2A shows a distal portion of a medical device.

As shown in FIG. 1, for example, the controller 104 may include one or more actuators, e.g., first and second actuators 136, 138, each coupled to at least one control member 282 (e.g., mechanical or electronic steering wire) that extends along the shaft 102 (see FIG. 2A). In some embodiments, the first actuator 136 may control deflection of the distal end 124 of the shaft 102 in one plane (e.g., xy plane), and the second actuator 138 may control deflection of the distal end 124 in a different plane (e.g., yz plane). For example, the first actuator 136 may be coupled to a first pair of control members 282 such that rotational and/or translational motion of the first actuator 136 may deflect the distal end 124 of the shaft 102 in one plane. Similarly, the second actuator 138 may be coupled to a second pair of control members 282, such that rotational and/or longitudinal motion of the second actuator 138, independent of the first actuator 136, may deflect the distal end 124 in a different plane. Concerted movement of the first and second actuators 136, 138 may achieve deflection in a plurality of other planes, e.g., providing for 360 degree manipulation of the shaft 102. In some embodiments, each actuator 136, 138 may be coupled to only one control member 282 and/or the controller 104 may include only one actuator.

Other steering mechanisms suitable for manipulating the shaft 102 may be used, including, but not limited to, other types of mechanical mechanisms and electrical mechanisms. For example, the controller 104 may be in electrical communication with various portions of the shaft 102 (e.g., via electronic control members 282), such that user input at the actuators 136, 138 may be converted to electrical signals to control deflection of the distal end 124 of the shaft 102. In some embodiments, the medical device 100 may not include a steering mechanism. For example, the medical device 100 need not be steerable according to some aspects of the present disclosure.

Figure 2B:
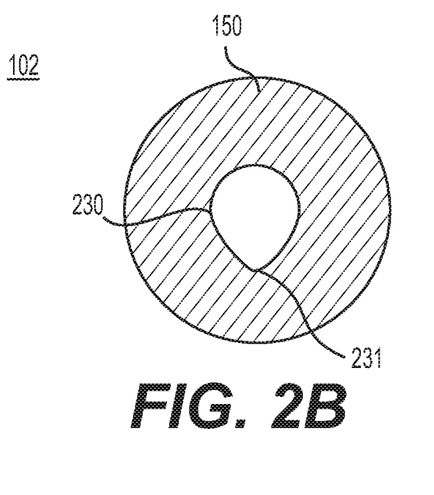
FIGS. 2B and 2C show cross-sectional views of FIG. 2A.
Figure 2C:
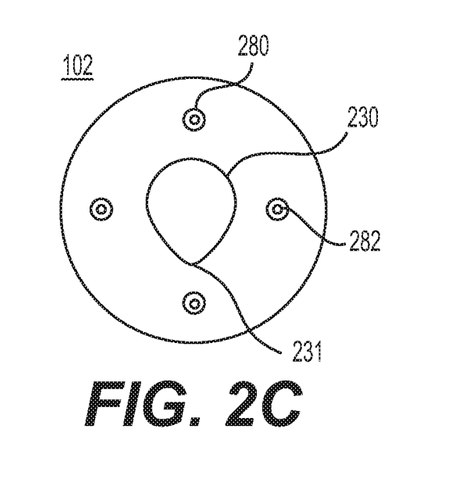

The shaft 102 may include one or more working channels 230 and/or one or more auxiliary channels 280. An example is illustrated in FIGS. 2A-2C, wherein FIG. 2B shows a cross-sectional view of a distal portion of the shaft 102 of FIG. 2A, and FIG. 2C shows a cross-sectional view of a proximal portion of the shaft 102 of FIG. 2A. In some embodiments, for example, the shaft 102 may include one working channel 230 and four auxiliary channels 280 as shown. While FIGS. 2A-2C show the shaft 102 including one working channel 230 and four auxiliary channels 280, the shaft 102 may include more than one working channel (e.g., two, three, or more working channels). Further, the shaft 102 may include fewer or more than four auxiliary channels 280 (e.g., two, three, five, or six or more auxiliary channels 280), or may not include any auxiliary channels 280.

The working channel 230 may receive one or more instruments inserted into the working channel 230 for performing a medical procedure. Suitable instruments may include, but are not limited to, needle devices, forceps, scalpels, snares, biopsy brushes, optical devices, and imaging devices (e.g., in addition to the ultrasound sensor(s)). The working channel 230 may extend from the proximal end 122 of the shaft to the distal end 124, and may be in communication with a proximal inlet for insertion of the instruments. For example, the medical device 100 may include a side port 144 (see FIG. 1) in communication with the working channel 230 for the insertion of one or more instruments into the working channel 230.

In some embodiments, the working channel 230 may be configured to maintain one or more instruments in a specific orientation with respect to the shaft 102. For example, the working channel 230 may have a cross-sectional shape and/or one or more surface features complementary to the instrument to "key" the instrument to the working channel and limit relative rotation between the instrument and the working channel. The working channel 230 may have a non-circular cross-sectional shape as shown in FIGS. 2B and 2C, e.g., having a tapered or narrowed portion 231. An instrument having a complementary cross-sectional shape may maintain its orientation as it passes through the working channel 230. The distal end of the instrument therefore may have a unique radial location upon exiting the distal end 124 of the shaft 102. By aligning the shaft 102 with a target site (e.g., positioning the shaft 102 such that the narrowed portion 231 of the working channel 230 points toward the target site), the instrument may have the proper orientation for performing a medical procedure at the target site.

In some embodiments, the shaft 102 may include an area 211 having a unique echogenic pattern or signature to assist in directing the instrument(s) towards the target site. Any suitable material, combination of materials, surface features, and/or texture may be used to produce a unique echogenic signature to be identified in an ultrasound image. For example, the area 211 may include grooves, divots, lattice marks, stepped portions, projections, ridges, and/or other distinguishing surface features or textures. Further, for example, the area 211 may comprise one or more materials having a different density than other portions of the shaft 102, such that the area 211 may be identified in an ultrasound image.

The area 211 may be integrated into the shaft 102 (e.g., integrated into the ultrasound sensor 150 or other distal portion of the shaft 102) in order to have a fixed position with respect to the working channel 230. Upon locating a target site in the body via ultrasound imaging, the area 211 (also visible via ultrasound) may be aligned with the target site to likewise align the working channel 230 (and, for example, narrowed portion 231) with the target site. Instruments inserted into the working channel 230 and maintaining a specific orientation as they pass through the working channel 230 therefore may have the proper orientation for performing a medical procedure at the target site.

The auxiliary channels 280 may accommodate control members 282 for deflecting the shaft 102, as mentioned above, and/or for connecting the ultrasound sensor 150 to a power source or for electronic communication. In some embodiments, the auxiliary channels 280 and/or control members 282 may terminate proximal to the ultrasound sensor 150, as shown in FIG. 2A. Each auxiliary channel 280 may house one or more control members 282. Further referring to FIGS. 2A and 2C, for example, two of the auxiliary channels 280 may accommodate a pair of control members 282 coupled to the first actuator 136, and the remaining two auxiliary channels may accommodate a separate pair of control members 282 coupled to the second actuator 138 (only one control member 282 is shown in FIG. 2A for clarity). One of the auxiliary channels 280 also may accommodate an electronic control member 282 to couple the ultrasound sensor 150 to a power source, a processor for generating images, and/or a graphical interface for displaying images.

Ultrasound Sensors

The ultrasound sensor(s) may be in wired or wireless communication with a processor for analyzing the ultrasound signals to produce an image. In some embodiments, for example, the ultrasound sensor(s) may be configured to communicate with a processor such as a computer via an electronic cable, as mentioned above. In some embodiments, the medical device may include a processor. Referring to FIG. 1, for example, the medical device 100 may include a processor in the controller 104, the shaft 102, or the ultrasound sensor 150. Further, the processor may be in wired or wireless communication with a suitable graphical interface to display the images generated via the ultrasound sensor(s).

In some embodiments, the ultrasound sensor(s) may completely surround the working channel. The ultrasound sensor may include a single sensor partially or completely surrounding the working channel, or a plurality of sensors disposed around the working channel such that the plurality of sensors partially or completely surround the working channel.

The ultrasound sensor(s) may be fixed with respect to the working channel (e.g., incorporated into the wall of the shaft or otherwise immovable relative to the working channel), while instruments may be translatable through the working channel and relative to the ultrasound sensor(s). In some embodiments, the ultrasound sensor(s) may at least partially surround the working channel(s) of the medical device, e.g., to allow a user to view sites of interest in the body while independently and simultaneously manipulating instruments passed through the working channel(s). The ultrasound sensor(s) may be configured to image a single field of view greater than about 90 degrees, greater than about 180 degrees, greater than about 270 degrees, or a single field of view of about 360 degrees (panoramic view) about the shaft. Thus, for example, the ultrasound sensor(s) may provide a relatively wide field of view in a single image (e.g., the entire image captured simultaneously), rather than patching together images captured in sequence with a more narrow field of view. By including a relatively wide field of view in a single image, the ultrasound sensor(s) may help to guide the user in performing a medical procedure.

Figure 3A:
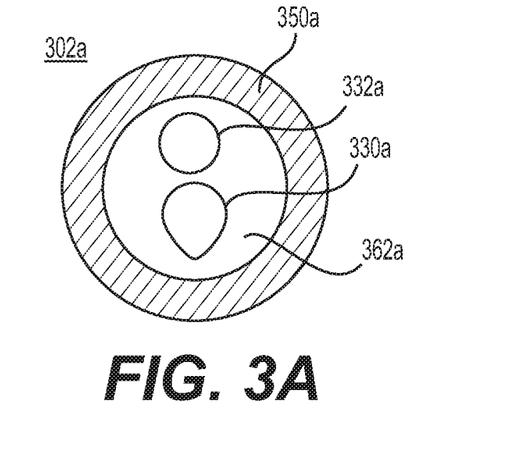
FIGS. 3A and 3B show cross-sections of medical devices, in accordance with embodiments of the present disclosure.

FIGS. 2A-2B and FIG. 3A illustrate examples of medical devices comprising a single ultrasound sensor. For example, FIGS. 2A-2B show a single ultrasound sensor 150 that includes a lumen therethrough to define or otherwise accommodate the working channel 230, such that the ultrasound sensor 150 completely surrounds the working channel 230. In some embodiments, the shaft may include a wall separating at least part of the lumen of the ultrasound sensor from one or more working channels. FIG. 3A illustrates a cross-sectional view of a shaft 302a (which may include any of the features of shaft 102 discussed above) comprising a single ultrasound sensor 350a disposed radially outward of, and completely surrounding, two working channels 330a, 332a. As shown, a wall portion 362a separates the ultrasound sensor 350a from the working channels 330a, 332a. At least one of the working channels (e.g., working channel 330a) may be configured to maintain instruments in a particular orientation upon exiting the distal end of the shaft 302a, as discussed above. In some embodiments, both working channels 330a, 332a may be configured to maintain the orientation of instruments as they are passed through the respective working channels. The shaft may include only one working channel (e.g., 330a), or include more than two working channels, such as three or more working channels.

While FIGS. 2A-2C and FIG. 3A illustrate examples of devices comprising a single ultrasound sensor, additional embodiments are encompassed within the present disclosure. For example, a single ultrasound sensor need not completely surround the working channel(s). In some embodiments, the ultrasound sensor may form an arc that only partially surrounds the working channel(s).

In some embodiments, the medical device may comprise a plurality of ultrasound sensors, e.g., two, three, four, five, or six or more sensors. The ultrasound sensors may be configured to produce individual images (e.g., arc-shaped images), and/or may be combined to generate a single field of view. In some embodiments, for example, the plurality of ultrasound sensors may provide for a 360 degree view. The individual images may be captured simultaneously and/or may be combined simultaneously into a single image.

Figure 3B:
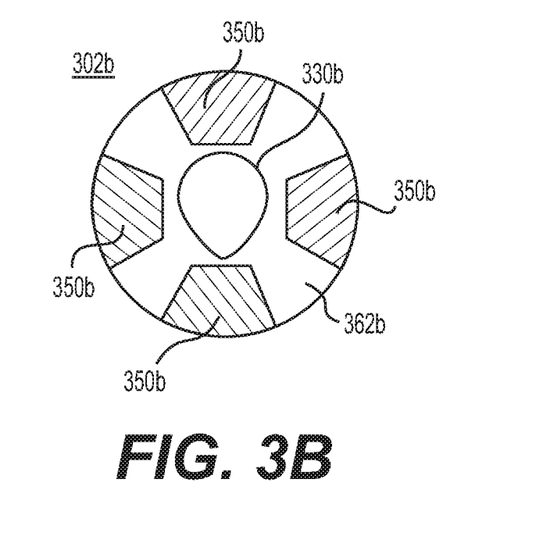

FIG. 3B illustrates a cross-sectional view of a shaft 302b (which may include any of the features of elongate bodies 102 or 302a discussed above) comprising four ultrasound sensors 350b disposed radially outward of the working channel 330b. The sensors 350b may be disposed within a wall portion 362b of the shaft 302b. In some embodiments, the plurality of sensors 350b may be regularly spaced (e.g., symmetrically spaced) about the working channel 330b. The wall portion 362b may separate each ultrasound sensor 350b from the working channel 330b and/or from adjacent ultrasound sensors 350b.

Instruments

As mentioned above, the instruments used for performing a medical procedure according to the present disclosure may have a shape complementary to the shape of the working channel. With respect to the shaft 102 shown in FIGS. 2A-2C, for example, the instruments to be inserted into the working channel 230 may include a shaft that has a complementary non-circular cross-sectional shape, such that once inserted into the working channel 230, the instruments cannot rotate relative to the working channel 230 and maintain their radial orientation.

The instruments may have a preset or predetermined shape, such that the distal end of the instruments curve or bend radially outward upon exiting the working channel of the medical device. For example, the instruments may have a preset curved configuration wherein the distal end of the instrument bends back proximally. In some embodiments, the instrument may comprise a flexible material, e.g., a shape-memory material such as Nitinol, that allows the instrument to have a straight configuration while housed in the working channel, and a curved configuration outside the working channel. When the instrument exits the working channel to adopt the preset curved configuration, the distal end of the instrument may come within the field of view of the ultrasound sensor(s).

Figure 4A:
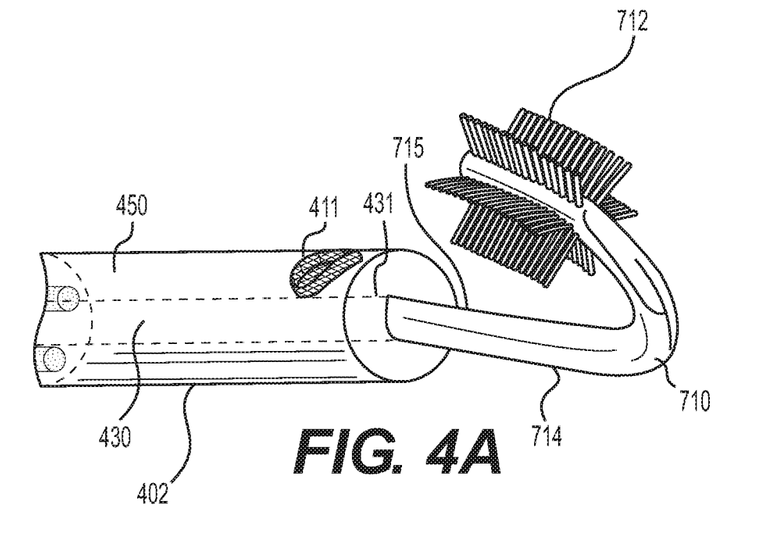
FIGS. 4A and 4B show exemplary instruments, in accordance with one or more embodiments of the present disclosure.
Figure 4B:
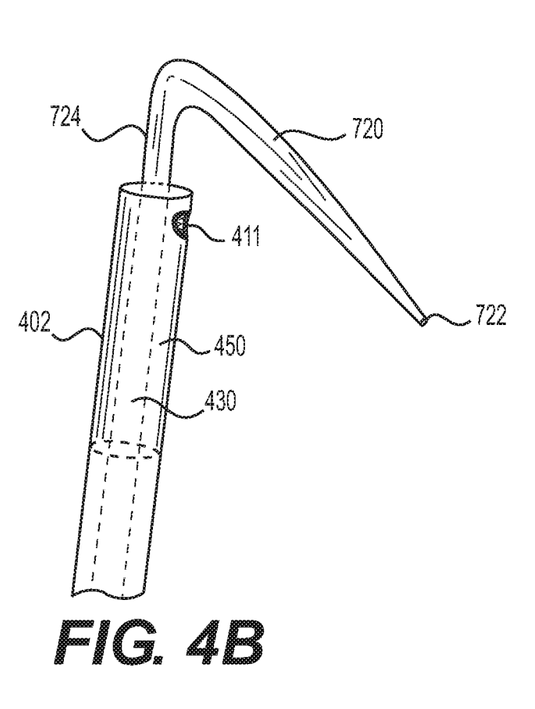

FIGS. 4A and 4B show instruments according to some embodiments of the present disclosure, wherein FIG. 4A shows a biopsy brush 710, and FIG. 4B shows a needle. Other types of instruments are encompassed by the present disclosure, as mentioned above. Each instrument 710, 720 is shown extending through the working channel 430 of an exemplary shaft 402 (which may include any of the features of shafts 102, 302a, or 302b discussed above) comprising a working channel 430 and an ultrasound sensor radially outward of the working channel 430. The working channel 430 has a narrowed portion 431, similar to the shape of working channel 230 shown in FIGS. 2A-2C. Further, the shaft 402 includes an area 411 with a unique echogenic signature, similar to area 211 of shaft 102 shown in FIGS. 2A-2C, wherein the area 411 is radially aligned with the narrowed portion 431 of the working channel 430.

Referring to FIG. 4A, the brush 710 may have a body 714 with a narrowed portion 715 complementary to the narrowed portion of the working channel 430, such that, once inserted into the working channel 430, the brush 710 cannot rotate about an axis of working channel 430 to change its orientation. The distal end 712 of the brush 710 may be preshaped into a curved configuration, such that the distal end 712 bends back proximally, aligned with the narrowed portion 715. The brush 710 may comprise a flexible material that allows the distal end 712 to adopt a linear configuration for insertion into the working channel 430 until exiting the working channel 430 as shown. While in the curved configuration, the distal end 712 of the brush 410 may point towards the echogenic area 411 of the shaft 402. The curvature may allow the distal end 712 of the brush 710 to bend back and into the field of view of the ultrasound sensor 450. The distal end 712 of the brush may extend radially outward and include bristles for collecting tissue samples from within a patient's body, e.g., from a tissue surface adjacent to the shaft 402.

FIG. 4B shows a needle 720 extending through the working channel 430, wherein the needle has a pointed distal end 722 for sampling tissue. The body 724 of the needle 720 also may have a shape complementary to the working channel 430, e.g., in order to "key" the needle 720 to the working channel 430 to maintain its orientation relative to the shaft 402. Similar to the brush 710 of FIG. 4A, the needle 720 may have a preset curved configuration, such that upon exiting the working channel 430, the distal end 722 of the needle 720 may point towards the echogenic area 411 of the shaft 402, and may bend back within view of the ultrasonic sensor 450.

The medical devices and instruments disclosed herein may be used to image and/or conduct medical procedures on any suitable passageway, channel, structure, or surface within the body, including, but not limited to, features of the respiratory system, the gastrointestinal system, and/or the cardiovascular system. In some embodiments, for example, the medical device may be used in endobronchial ultrasound (EBUS) procedures to view various features of the respiratory system. In this procedure, an endoscopic ultrasound probe is introduced into the trachea and advanced into the bronchus and bronchial passageways for analysis, e.g., to locate and/or identify abnormalities such as lesions or enlarged lymph nodes, which may be located beyond the inner bronchial wall. EBUS may be used to image tracheo-bronchial lymph nodes to screen for lung cancer, for example, wherein ultrasound allows visualization of diseased or otherwise abnormal tissues outside of the bronchial airways.

Figure 5A:
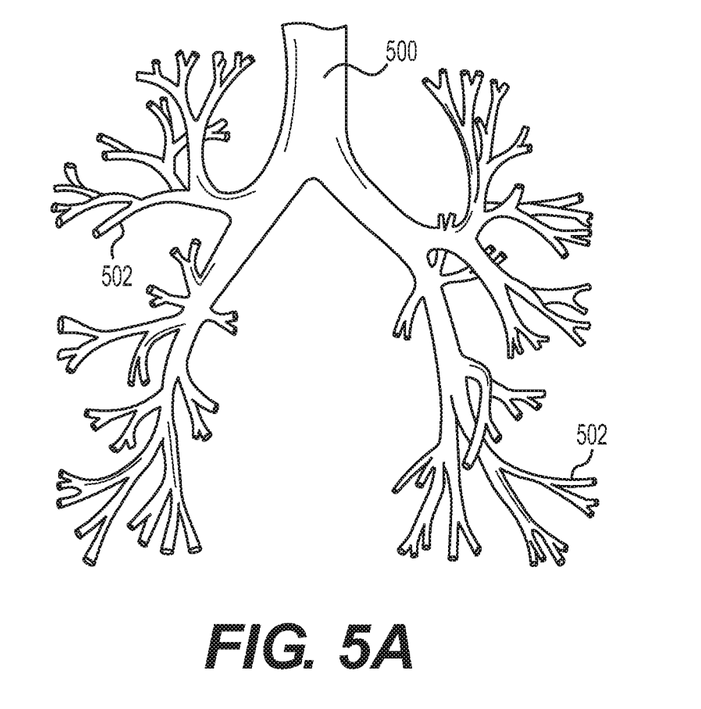
FIG. 5A shows bronchial passageways of a patient.
Figure 5B:
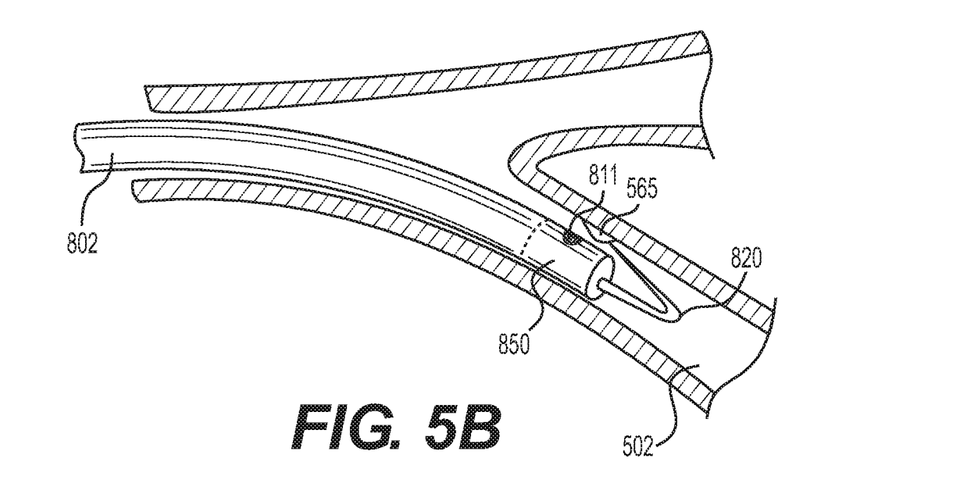
FIG. 5B illustrates a medical procedure within a bronchial passageway, in accordance with one or more embodiments of the present disclosure.

FIGS. 5A and 5B illustrate an exemplary EBUS procedure using the devices and instruments of the present disclosure. FIG. 5A shows the bronchus of a patient, including various bronchial passageways 502. The shaft 802 of a medical device (which may include any of the features of shafts 102, 302a, 302b, and/or 402, or medical device 100 discussed above) may be inserted into the bronchus 500 and advanced into a bronchial passageway 502 as shown in FIG. 5B. The shaft 802 may include an ultrasound sensor 850 (which may include any of the features of ultrasound sensors 150, 350a, 350b, and/or 450 discussed above), such that the ultrasound sensor 850 partially or completely contacts the walls of the bronchial passageway 502 to facilitate imaging. The ultrasound sensor 850 may be used to generate images of the passageway 502, and/or of anatomical features deeper in the anatomy (beyond the walls of passageway 502) in real time as the shaft 802 is moved along the passageway 502. The shaft 802 may include an area 811 with a specific echogenic signature visible in the images.

Upon locating a site of interest, e.g., lesion 565, along the surface of the passageway 502 or even deeper than the surface of passageway 502, the shaft 802 may be positioned (e.g., translated and/or rotated) such that the lesion 565 is radially aligned with the area 811 on the shaft 802. An instrument 820 (which may include any of the features of instruments 710 and/or 720 discussed above) such as a biopsy needle may be inserted into the shaft 802 via a working channel of the shaft 802, wherein upon exiting the working channel, the distal end of the instrument 820 may bend back proximally to come within the field of view of the ultrasound sensor 850. The distal end of the instrument 820 also may be aligned with the lesion 565 to collect a tissue sample for analysis. Upon collecting the sample, the instrument 820 may be withdrawn into the working channel (e.g., by bending the distal end of the instrument 820 into a linear configuration for passage through the working channel), and withdrawn from the patient's body.

Other embodiments of the present disclosure will be apparent to those skilled in the art from consideration of the specification and practice of the embodiments disclosed herein. While certain features of the present disclosure are discussed within the context of exemplary procedures (e.g., EBUS and biopsy procedures), the devices, instruments, and methods are not so limited and may be used in other areas of the body, and for other medical procedures according to the general principles disclosed. It is intended that the specification and examples be considered as exemplary only, with a true scope and spirit of the present disclosure being indicated by the following claims.

We claim:

1. A medical device comprising:
   a shaft including a working channel extending from a proximal end of the shaft to a distal end of the shaft, wherein the working channel includes a narrowed portion extending from the proximal end of the shaft to the distal end of the shaft;
   an ultrasound sensor disposed radially outward of a distal portion of the working channel such that the ultrasound sensor at least partially surrounds the working channel at or adjacent to the distal end of the shaft, wherein the ultrasound sensor includes an area configured to indicate an orientation of the narrowed portion of the working channel in ultrasound images generated by the ultrasound sensor;
   an instrument extendable through the working channel of the shaft, wherein, while the instrument is in a deployed position, a distal end of the instrument extends outside of the shaft and has a fixed radial position relative to the shaft; and
   wherein the area is radially fixed relative to the distal end of the instrument while in the deployed position, and wherein the instrument is shaped such that the narrowed portion of the working channel orients the distal end of the instrument with the area.

2. The medical device of claim 1, wherein:
   the working channel is configured to prevent rotation of the instrument relative to the shaft when the instrument is in the deployed position.

3. The medical device of claim 2, wherein the instrument is translatable from the proximal end of the shaft to the distal end of the shaft, wherein the instrument comprises a flexible material and has a preset curved configuration, such that the distal end of the instrument has a substantially straight configuration within the working channel and the curved configuration outside the working channel.

4. The medical device of claim 1, wherein the working channel has a non-circular cross-sectional area to prevent rotation of the instrument within the working channel.

5. The medical device of claim 1, wherein the ultrasound sensor includes a plurality of ultrasound sensors disposed about the working channel to at least partially surround the working channel.

6. The medical device of claim 5, wherein the plurality of ultrasound sensors are spaced at regular intervals about a perimeter of the shaft.

7. The medical device of claim 5, wherein the working channel is a first working channel, the medical device further comprising a second working channel radially inward of the ultrasound sensor, wherein the ultrasound sensor is configured to image a single field of view greater than 180 degrees.

8. The medical device of claim 5, wherein the ultrasound sensor is configured to image a single field of view of 360 degrees.

9. The medical device of claim 1, wherein the ultrasound sensor completely surrounds the working channel.

10. The medical device of claim 1, wherein the ultrasound sensor includes a single sensor.

11. The medical device of claim 1, further comprising a controller coupled to the proximal end of the shaft and a plurality of control members for deflecting the distal end of the shaft in at least two different planes.

12. The medical device of claim 1, wherein the area extends around less than an entirety of a circumference of the shaft.

13. The medical device of claim 12, wherein, while the instrument is in the deployed position, the distal end of the instrument extends along a first axis and is prevented from rotating relative to the shaft, wherein the area is fixed relative to the first axis, and wherein the instrument is movable between the deployed position and an undeployed position where the distal end of the instrument is disposed within the working channel.

14. The medical device of claim 1, wherein, while the instrument is in the deployed position, the distal end of the instrument extends along a first axis, wherein the area is fixed relative to the first axis.

15. The medical device of claim 1, wherein the instrument is movable between the deployed position and an undeployed position where the distal end of the instrument is disposed within the working channel.

16. A medical device comprising:
    a shaft including a working channel extending from a proximal end of the shaft to a distal end of the shaft, wherein the working channel includes a narrowed portion extending from the proximal end of the shaft to the distal end of the shaft;
    an ultrasound sensor radially outward of a distal portion of the working channel, wherein the ultrasound sensor includes an area configured to indicate an orientation of the narrowed portion of the working channel in ultrasound images generated by the ultrasound sensor;
    a needle extendable through the working channel, wherein, in a deployed position, a distal end of the needle extends outside of the shaft and has a fixed radial position relative to the shaft; and
    the area extending only partially around a circumference of the shaft, wherein the needle is shaped such that the narrowed portion of the working channel orients the distal end of the needle with the area.

17. The medical device of claim 16, further comprising:
a controller coupled to the proximal end of the shaft for deflecting the distal end of the shaft in at least two different planes; and
a plurality of control members extending from the controller to a portion of the shaft proximal to the ultrasound sensor.

18. The medical device of claim 16, wherein the ultrasound sensor completely surrounds the working channel, wherein the ultrasound sensor is configured to image a single field of view of 360 degrees.

19. A method of treating a patient, the method comprising:
inserting a shaft of a medical device into a passageway of the patient, the shaft including:
a working channel extending from a proximal end of the shaft to a distal end of the shaft, wherein the working channel includes a narrowed portion extending from the proximal end of the shaft to the distal end of the shaft;
an ultrasound sensor disposed radially outward of a distal portion of the working channel such that the ultrasound sensor at least partially surrounds the working channel at or adjacent to the distal end of the shaft, wherein the ultrasound sensor includes an area configured to indicate an orientation of the narrowed portion of the working channel in ultrasound images generated by the ultrasound sensor; and
generating at least one image with the ultrasound sensor, wherein the area indicates the orientation of the working channel in the at least one image;
using the at least one image to radially align the area with a target site in the patient; and
after aligning the area with the target site, inserting an instrument through the working channel and out of the distal end of the shaft, into the patient and into a fixed radial position relative to the shaft, wherein the fixed radial position and the area are radially fixed relative to one another and the instrument is shaped such that the narrowed portion of the working channel orients the distal end of the instrument with the area.

20. The method of claim 19, further comprising:
manipulating the instrument to conduct a medical procedure on the passageway while generating the image.

* * * * *